United States Patent [19]

Copes

[11] Patent Number: 5,030,239
[45] Date of Patent: Jul. 9, 1991

[54] BIOMECHANICAL ANKLE

[75] Inventor: Arthur Copes, Gonzales, La.

[73] Assignee: Copes, Inc., Baton Rouge, La.

[21] Appl. No.: 588,481

[22] Filed: Mar. 12, 1984

Related U.S. Application Data

[63] Continuation-in-part of Ser. No. 348,244, Feb. 12, 1982, Pat. No. 4,442,554.

[51] Int. Cl.$^5$ .............................................. A61F 2/66
[52] U.S. Cl. .................................................. 623/52
[58] Field of Search ...................... 623/47, 48, 49, 50, 623/51, 52, 53, 54

[56] References Cited

U.S. PATENT DOCUMENTS

| | | | |
|---|---|---|---|
| 2,470,480 | 5/1949 | Fogg | 3/35 |
| 3,196,463 | 7/1965 | Farneth | 3/32 |
| 4,306,320 | 12/1981 | Delp | 3/31 |
| 4,442,554 | 4/1984 | Copes | 3/35 |

FOREIGN PATENT DOCUMENTS

| | | | |
|---|---|---|---|
| 883321 | 6/1953 | Fed. Rep. of Germany | 3/6 |
| 487389 | 7/1921 | France | 3/6 |

*Primary Examiner*—David J. Isabella
*Attorney, Agent, or Firm*—C. Emmett Pugh

[57] ABSTRACT

An improved biomechanical ankle is provided which imitates the three primary categories of movement in a human foot. Parallel sole and limb supporting plates are held in spaced relationship by an upright post. The limb supporting plate is connected to the post with a ball and socket joint. A helical spring is fixed between the plates to provide resilient support to the anterior portion of the foot in imitation of normal muscular control. The ball and socket joint, in cooperation with the spring, permits the biomechanical ankle to imitate the inversion-eversion, plantar flexion-dorsiflexion, and lateral rotation found in a normal human foot.

9 Claims, 6 Drawing Sheets

BIOMECHANICAL ANKLE

CROSS REFERENCE TO RELATED APPLICATION

This application is a continuation-in-part of co-pending U.S. patent application Ser. No. 348,284 filed Feb. 12, 1982, now U.S. Pat. No. 4,442,554, the disclosure of which is incorporated by reference as fully as if it appeared herein.

BACKGROUND OF THE INVENTION

1. Field of the Invention

The present invention relates to a prosthetic foot and more particularly to a prosthetic foot imitating the movement of the human foot about three axes.

2. Description of the Problem and Prior Art Solutions

The process of terrestrial locomotion in humans involves a complex interaction of muscular contractions around a variety of joints in the foot. The interaction of these complex movements gives the foot an ability to adapt to its external environment and permits travel with relative ease over a variety of terrestrial surroundings.

There are three primary categories of movement in the ankle and foot: dorsiflexion and plantar flexion, inversion and eversion, and lateral rotation.

Dorsiflexion and plantar flexion are defined as the upward-downward motion of the foot in a plane perpendicular to the line of forward progression. Dorsiflexion is the movement of the foot upwardly and plantar flexion is the movement of the foot downwardly around an axis running between the bony protuberances of the ankle (hereinafter the "ankle axis"). Movement of the ankle in this plane is possible through a range of approximately 70°, 20° of dorsiflexion and 50° of plantarflexion.

Eversion is defined as the moving of the sole of the foot outwardly at the ankle joint while inversion is defined as the moving of the sole of the foot inwardly at the ankle joint. These movements take place around the subtalar axis, which is somewhat parallel to the line of forward progression. More precisely, the subtalar axis extends from the lateral aspect of the heel to the medial aspect of the sole adjacent the big toe. In terms of anatomic structure, the motion here described takes place in the subtalor joint of the ankle/foot.

Movement about the subtalor axis may be analogized to that found in an oblique hinge in which outward rotation of a vertical hinge member results in inward rotation of a horizontal hinge member. Similarly, inward rotation of an upper hinge member results in outward rotation of a lower hinge member. Anatomically, the inward rotation of the foot so that the sole faces inwardly (inversion) occurs as a result of bones in the lower leg being rotated outwardly around an axis running longitudinally through the leg. Outward rotation of the foot so that the sole faces outwardly (eversion) occurs as a result of the inward rotation of the bones in the lower leg about a longitudinal axis through the leg. The typical range of inversion is 20°, while a typical range of eversion is 5°. This aspect of movement in the ankle/foot complex gives an individual the ability to walk on uneven terrestial surfaces and slopes without difficulty.

The third type of movement in the ankle and foot is lateral rotation, also known as tibia torsion motion. This action occurs through a transverse, oblique hinge action of the ankle and foot. Laterial rotation moves the foot through a vertical plane substantially parallel to the ground.

The complex interplay among the three categories of motion described above gives rise to the natural gait observed in terrestial locomotion in humans. The walking cycle begins when initial floor contact is made with, for example, the heel of the right foot. Progressive dorsiflexion occurs throughout the first 30% of the walking cycle until the right foot is substantially flat on the ground. Plantar flexion next occurs as the heel is lifted off the ground, such flexion reaching a maximum at 60% of the walking cycle at which time "liftoff" occurs and the right foot swings forward through a step. The process of plantar flexion-dorsiflexion here described continues through each successive step.

In addition to plantar flexion-dorsiflexion, the foot is also simultaneously experiencing inversion-eversion. The inversion-eversion movement causes initial floor contact to occur at the lateral aspect of the heel as heel contact of the right foot occurs. As plantar flexion progresses, the pressure on the sole shifts diagonally from the lateral aspect of the heel to the medial aspect of the sole adjacent the big toe just as liftoff occurs. More precisely, inversion occurs until approximately 40% of the walking cycle has been completed, at which time eversion is experienced to transfer weight to the medial aspect of the foot to prepare for liftoff and swinging of the leg through a step.

If the foot were only permitted to move through a horizontal plane (dorsiflexion-plantar flexion) and about the subtalar axis (inversion-eversion), the foot would be limited in its adaption to the variety of terrains over which locomotion could smoothly occur. It is fortunate, therefore, that the human foot is also provided with lateral rotation, or movement through a horizontal plane about an imaginary axis running vertically through the leg and heel. This third motion enhances the fluidity of locomotion by permitting the smooth transfer of weight through an arc running diaganolly across the sole from the outside rear heel to the inside of the sole adjacent the big toe.

It is therefore desirable that a biomechanical ankle be provided which will imitate all three of the basic movements of the ankle and foot described above.

PRIOR ART STATEMENT

Characterizing the closest prior art of which the applicant is aware, attention is invited to the following United States Patent Numbers:

Delp U.S. Pat. No. 4,306,320;
May U.S. Pat. No. 3,874,004;
Simonsson U.S. Pat. No. 2,098,067;
Peer U.S. Pat. No. 710,996;
Parmelee U.S. Pat. No. 37,637.
Dumelin U.S Pat. No. 2 368,917.

Delp is considered relevant since it shows a ball and socket joint which permits opposing wedges to be adjusted so as to selectively adjust the degree of arch in the sole of a prosthetic foot. This arrangement is designed to adapt the foot to shoes having heels of different heights. It does not, however, imitate the movement of the foot in the three aspects described above.

May discloses an artificial ankle joint which is suitable for patients who have undergone the Symes amputation. A sole plate is provided having posterior and anterior, upwardly sloping pivot joints with a rubber block situated therebetween to assist in the transfer of weight from the posterior to the anterior part of the foot. Such a device requires the wearer to use a series of upper thigh and lower thoracic muscles to lift the leg and implant the foot. Normal locomotion is impeded because the links for A and B of May would swing a foot in relation to a leg in such a manner as to make it slide along a walking surface. This structure also fails to provide a stable support for the anterior portion of the foot, which would result in impaired locomotion. The only natural movement permitted by May is plantar flexion and dorsiflexion, and it is further limited in that it is specifically useful only with a Symes amputation.

Dumelin U.S. Pat. No. 2,368,917 teaches a structure in which plantar flexion-dorsiflexion may be possible, but the somewhat horizontal planes which pivot about a ball are much too close to give an inversion-eversion effect.

The patent issued to Simonsson, U.S. Pat. No. 2,098,067 does appear to permit some degree of inversion-eversion, but such movements are uncontrolled and would therefore impart a certain wobble to the wearer's gait.

U.S. Pat. Nos. 710,996 and 37,637 also disclose structures having some sort of a ball joint, but these structures also lack the ability to imitate the three aspects of primary motion in the ankle and foot. In addition, these prior art structures lack any means for providing a fixed type of support for the anterior portion of the foot.

The prior art also includes prosthetic foot structures differing from those shown in these patents. One such alternative foot is known as the solid ankle cushion heel (SACH) which is made of a solid material and does not give a patient controlled motion of the foot.

Another prior art structure is a single axis foot, such as that produced by OAAO Bock. Artificial feet of this type have only a single axis of rotation, thereby poorly imitating the movement of a human ankle. The Bock foot is also bulky, therefore making it useful only in above the knee amputations. It is not compact enough to sit underneath the stump of a Symes amputation, which involves amputation of only the foot.

It is accordingly, an object of the present invention to provide an improved artificial ankle and foot which imitate the natural motion of the human foot with respect to dorsiflexion-plantarflexion, inversion-eversion, and lateral rotation.

Another object is to provide a prosthetic ankle which is durable, lightweight, capable of supporting tremendous weight and torque forces, and which compresses and moves dynamically in a fashion similar to the normal foot.

It is another object of the invention to provide a biomechanical ankle which is small enough to be acceptable for cosmetic purposes.

It is similarly desirable that the ankle joint permit patients to develop a normal gait with the least amount of energy expenditure.

SUMMARY OF THE INVENTION

The present invention has achieved these objects and overcome the significant drawbacks of the prior art by providing a biomechanical ankle for use in an artificial foot which is adapted for attachment to an amputee. The biomechanical ankle is comprised of a flat sole plate and a limb supporting plate held in spaced, parallel relationship to each other by an upright post. The post and limb supporting plate are coupled with a ball and socket joint to permit rotation of the plates in any direction about the post. A helical spring coil is provided anterior to the post and is fixed between the base and limb supporting plates to provide a controllable, resilient support for the anterior portion of the foot. The use of such a spring gives the wearer of the artificial foot an enhanced ability to control locomotion with the muscles which are usually employed in walking.

The upright post and ball joint are, in preferred embodiments, located 3–7 millimeters posteriorly to the trochanter-knee-ankle (TKA) alignment of the person wearing the artificial foot. The TKA line refers to the imaginary line which intersects the greater trochanter ("hip bone"), knee and ankle when a person is standing in a neutral, upright position. Placement of the post substantially colinearly with the TKA line provides a biomechanically proper pivot point about which movement of the foot may occur.

In other preferred embodiments, the longitudinal axis of the helical coil which is fixed between the sole plate and supporting plate is offset from the vertical plane by five to ten degrees, the superior edge of the spring inclining towards the medial aspect of the wearer's body. The slope of the spring causes the longitudinal axis of the elongated rectangular top plate to intersect the longitudinal axis of the elongated, rectangular lower sole plate at 5° to 10°. This relationship of the plates and spring facilitates the arc-like transfer of weight on the sole of the foot along the subtalar axis.

Another characteristic of this invention is that the screw threaded stud which is used to attach the ankle to the amputee, or his artificial limb, is provided with means for adjusting the position of the stud along the longitudinal axis of the upper, supporting plate. This feature permits the point of attachment between the wearer and the supporting plate to be adjusted in accordance with the requirements of the wearer.

BRIEF DESCRIPTION OF THE DRAWINGS

FIG. 12 demonstrates eversion in a right foot viewed from the front, FIG. 14 demonstrates inversion of a right foot viewed from the front, and FIG. 13 demonstrates the neutral positon therebetween wherein the incline of the helical spring at rest is shown.

DESCRIPTION OF THE PREFERRED EMBODIMENT

Figure 1:
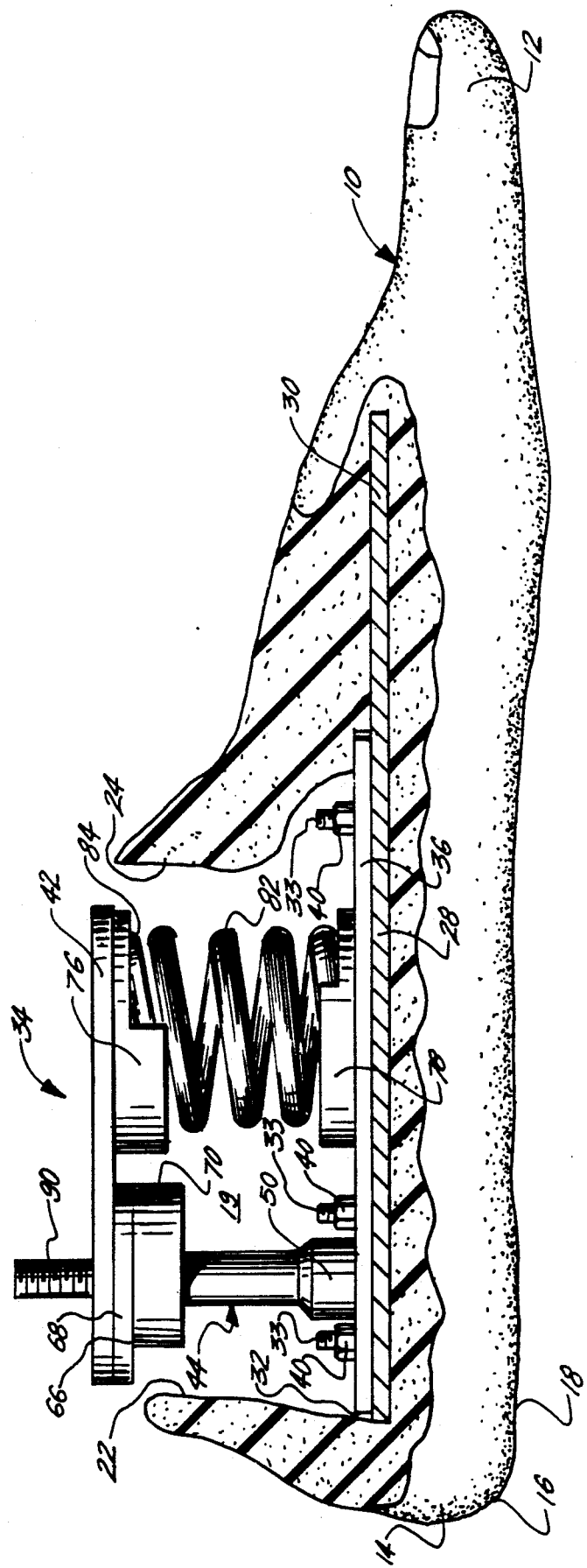
FIG. 1 is a vertical view of a prosthetic foot, portions being cut away for clarity, embodying the principles of the present invention.
Figure 2:
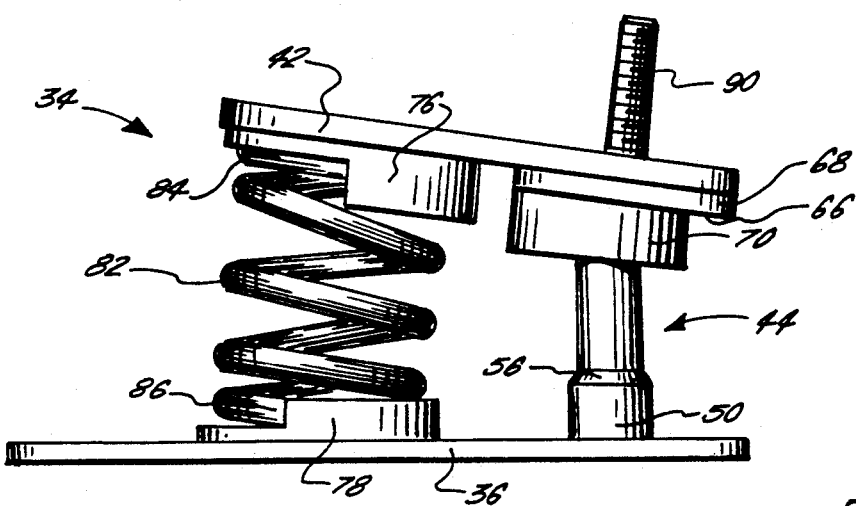
FIG. 2 is a side elevational view of the biomechanical ankle assembly showing the spring extended as would occur at the heel strike point during the walking cycle.
Figure 3:
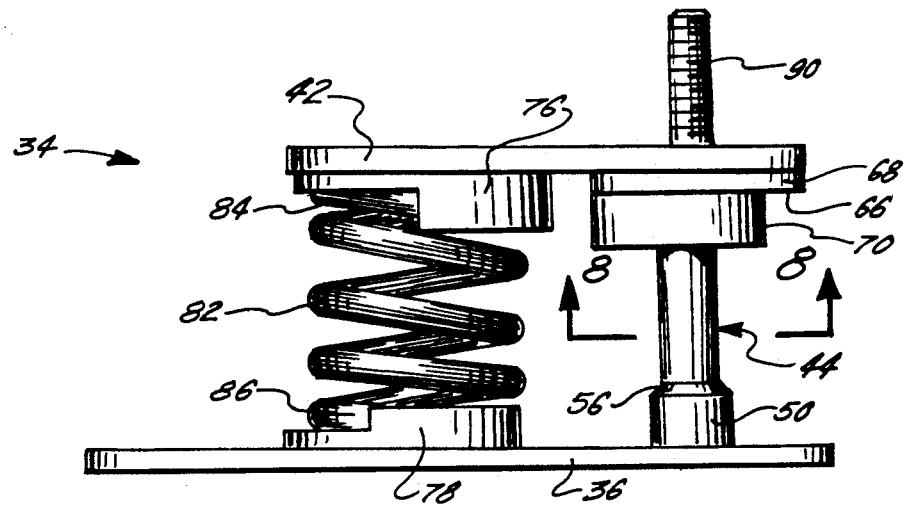
FIG. 3 is a side elevational view similar to FIG. 2 showing the spring in a neutral position.

Referring with greater particularity to the drawings, FIGS. 1-8 and 11-14 depict a first embodiment of a prosthetic foot and biomechanical ankle which embody the principles of the present invention.

The prosthetic foot 10 is made of a conventional soft, lightweight material, such as plastic, as is known in the art. The outside surface of foot 10 is configured to resemble the normal human foot having an anterior portion 12 at which toe-like structures are located and a posterior portion 14 configured to resemble a heel having an arcuate underside 16 and flat bottom 18.

Approximately the anterior half of foot 10 is solid and comprised of suitable plastic or foam-like material. The posterior portion of foot 10 is provided with a hollow, ankle-receiving cavity 19 which, in preferred embodiments, is defined by upwardly extending walls 22, 24 and a bottom (no number). An elongated base plate 28 is, in preferred embodiments, extended lengthwise along the longitudinal axis of the foot. Plate 28 has an embedded segment 30 which extends fixedly into the solid material of which foot 10 is made. Plate 28 is additionally provided with an anterior embedded segment 32, which in cooperation with segment 30 firmly anchors plate 28 in the bottom of cavity 19. Plate 28 is additionally provided with three pairs or side-by-side, upwardly extending bolts 34 (only three of which are shown in FIG. 1).

The biomechanical ankle itself is generally referred to by the reference numeral 34. Ankle 34 is comprised of a substantially flat, rectangular sole plate 36 which is elongated along the longitudinal axis of the foot 10. Base 28 and plate 36 are made of any strong, durable material such as steel, and their widths are no greater than the width of foot 10. Plate 36 is further provided with six bolt receiving apertures 38 (see FIGS. 5 and 11) which are positioned to be coaxially aligned with bolts 33 which are fixed in and project upwardly from plate 28. When plate 36 is positioned over base 20 such that bolts 33 project upwardly through appertures 38, nuts 40 can then be placed in fixed threaded engagement on threaded bolts 33 to firmly secure plate 36 to base 28.

A substantially rectangular, limb supporting plate 42, which is elongated along the longitudinal axis of the foot, is held in spaced, substantially parallel relationship to said plate 36 by an upright post 44. Plate 42 is of substantially the same width as plate 36, but the length of plate 42 is approximately three quarters the length of plate 36. Plate 42 is made of the same durable material of which plate 36 is made, which in preferred embodiments is steel. An elongated slot 46 is disposed longitudinally through the surface of plate 42 substantially coincidentally with the longitudinal midline of plate 42 (see FIGS. 6 and 11). Bolts 48 are placed through apertures (not shown) in plate 42 in order to removably affix plate 42 to the underlying structure of ankle 34 described below.

Figure 5:
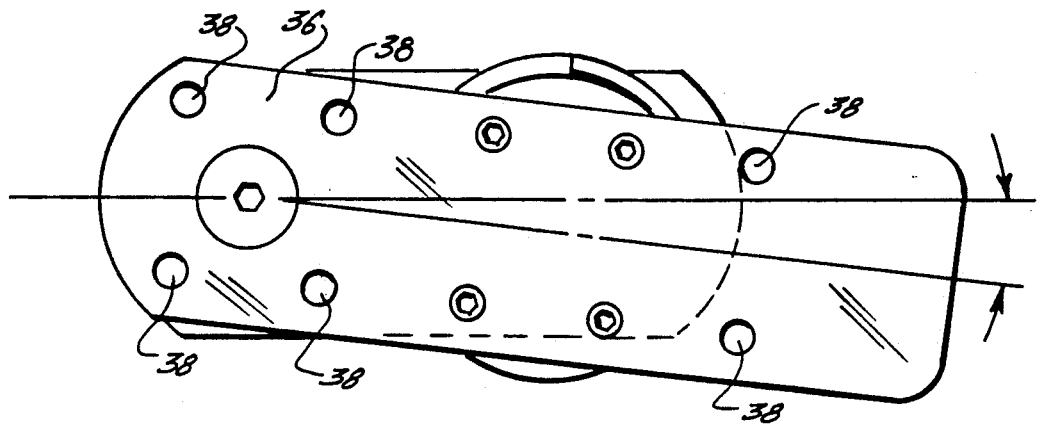
FIG. 5 is a bottom, plan view of the biomechanical ankle shown in FIGS. 2–4.

Post 44 has enlarged pedestal 50 which is fixed to plate 36 with bolt 52 (see FIG. 5). Post 44 tapers at shoulder 56 which results in post 44 having a reduced diameter at its superior portions. The post 44 is made of the same durable, relatively lightweight material as the other components of ankle 34, this material preferably being steel.

The position of post 44 within foot 10 provides another of the advantages of the instant invention. When a person assumes a neutral stance in which he is standing upright, a substantially straight line 58 can be drawn through the greater trochanter 60, knee 62 and ankle (not shown in FIG. 9). Line 54 is referred to in the art as the TKA line (trochanter-knee-ankle line). It has been found in the present invention that if post 44 is positioned substantially colinearly with the TKA line, a pivot point is established between plate 42 and post 44 at a natural position that approximates the pivot point in a human foot. It has been found especially beneficial to locate post 44 about 3-7 millimeters posterially to the TKA line 58.

Figure 6:
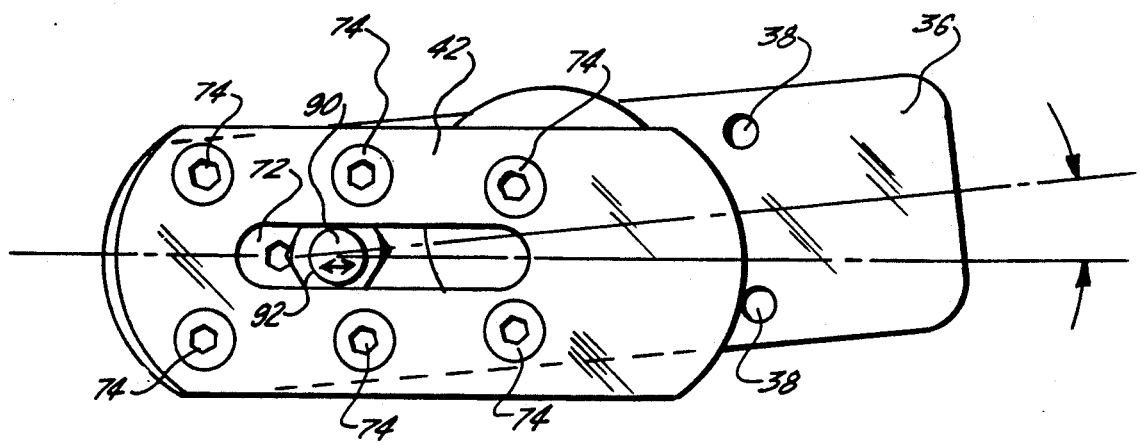
FIG. 6 is a top plan view of the biomechanical ankle shown in FIGS. 2–5.
Figure 8:
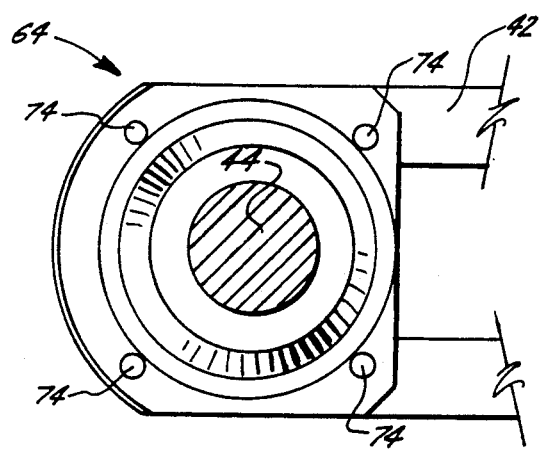
FIG. 8 is a cross-sectional view taken along section line 8—8 in FIG. 3.
Figure 10:
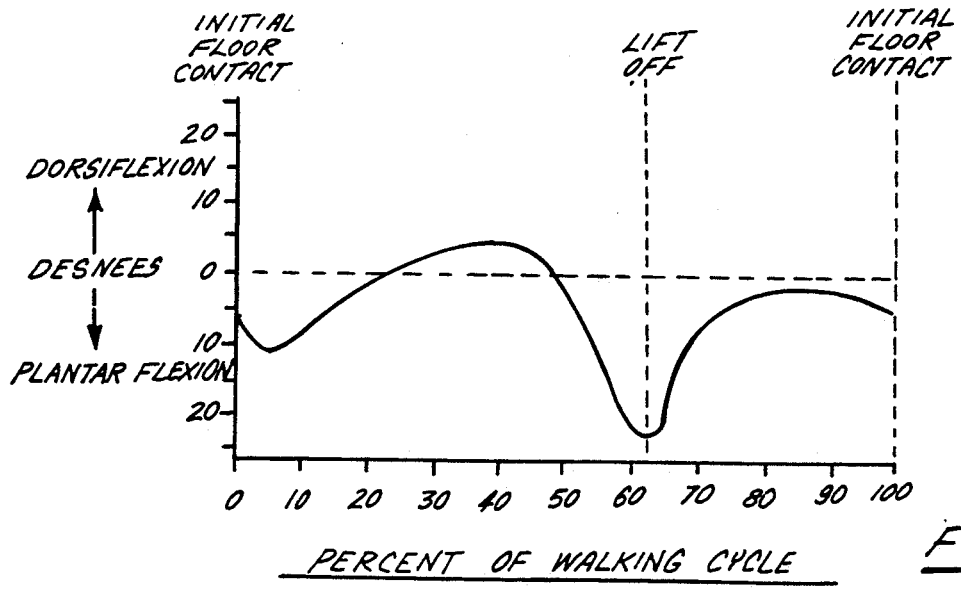
FIG. 10 is a graph showing the degrees of dorsiflexion and plantar flexion in a foot during the walking cycle.

Post 44 and plate 42 are coupled with a ball and socket joint generally referred to as 64 (see FIG. 8). Joint 64 is contained within housing 66 which is comprised of bolt receiving portion 68 and downwardly depending, joint covering skirt 70. A ball bearing (not shown) is contained in a space cooperatively defined by the cutaway interiors of portion 68 and skirt 70. The ball joint is of a conventional type which is not shown in the drawings. Access to the bearing is provided by access bolt 72 (FIG. 6). Access to bolt 72 can be obtained by selectively removing bolts 74 which selectively affix plate 42 to portion 68 of joint 64.

Plate 42 is provided with a downwardly depending collar 76 having a circular configuration and defining a round opening. Plate 36 is similarly provided with an identical but upwardly extending collar 78 which is also round and defines a circular opening 80 (see FIG. 7). Each of said collars 76, 78 is comprised of a semi-circular portion having a much narrower width than the remaining portion of the collar. This configuration gives rise to a flange 82 which defines a groove within each collar 76, 78.

A helical spring coil 82 is made of a resilient material such as steel and is substantially as long as the width between plates 36, 42. The superior edge 84 of coil 82 is positioned within the interior groove of collar 76. The inferior edge 86 (see especially FIGS. 11-14) is positioned within the interior groove of collar 78. Coil 82 is thereby held in fixed engagement between plates 36, 42. The longitudinal axis 88 of coil 82 (see FIG. 13) is offset from the vertical plane by 5° to 10°, preferred embodiments of the invention having an offset of 7°. The superior edge 84 inclines toward the medial aspect of the body.

Figure 11:
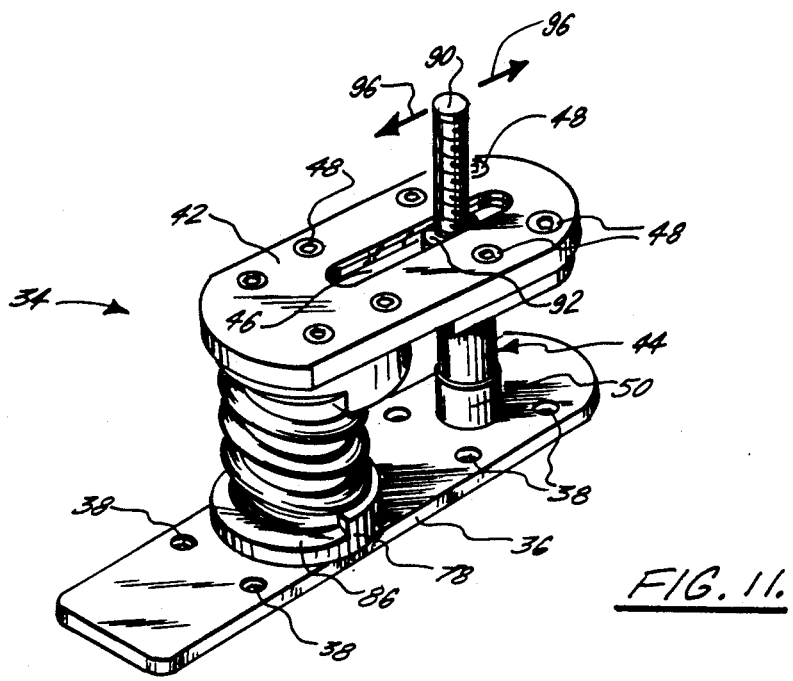
FIG. 11 is a perspective view of the biomechanical ankle of the present invention.

A screw threaded stud 90 is provided with an enlarged head 92 (see especially FIGS. 6 and 11) which is placed on the underface of plate 42, the threaded portion of stud 90 extending upwardly through slot 46 and beyond. Stud 90 is held in sliding engagement within slot 46 because the diameter of head 92 is greater than the width of slot 46, while the diameter of the upwardly extending portion of stud 90 is less than the width of slot 46. Stud 90 is used in attaching ankle 34 and foot 10 to the artificial limb or stump of the amputee wearing the foot 10. Stud 90 can move within slot 46 in the directions indicated by arrows 94, 96, (FIG. 11). Longitudinal movement of stud 90 within slot 46 provides a means for adjusting the point of attachment between the artificial limb and plate 42. The adjustability of this point of attachment is helpful since persons of varying weights require varying points of attachment. For example, a very obese person having a large concentration of body weight in the anterior aspects of the body could achieve more natural movement with the ankle if stud 90 were positioned slightly anteriorly to the position of post 44. However, a lighter person could more comfortably and naturally achieve locomotion if stud 90 were placed a few millimeters more in the anterior direction 94. Exact positioning of stud 90 is often a matter of trial and error, but the adjustability of the point of attachment represents a significant advance in the art of biomechanical ankles by recognizing the varying requirements of patients.

In operation, foot 10 is affixed to ankle 34 using nuts 40 threaded in snug engagement on bolts 33. Stud 90 is then fixedly attached to an artificial limb or human stump using tightened nuts (not shown) threaded on stud 90. The position of stud 90 within slot 46 is determined by calculation or trial and error positioning of stud 90 at different places in the directions of arrow 94 or 96.

Figure 4:
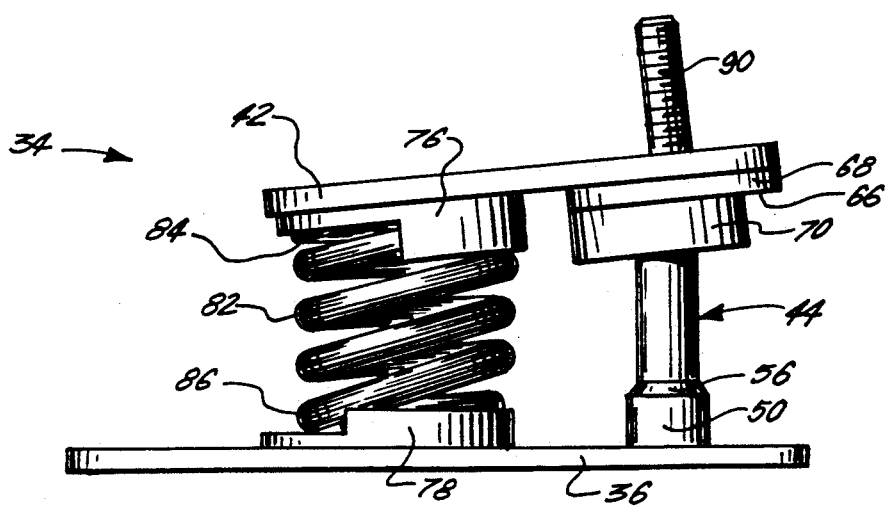
FIG. 4 is a side elevation view similar to FIG. 2 and 3 but showing the spring compressed as it may appear at the "toeoff" point in the walking cycle.

Once the foot 10 and ankle 34 are attached to the wearer, locomotion can begin. As previously explained, post 44 should in operation be disposed substantially colinearly with the trochanter-knee-ankle (TKA) line of the patient, preferably 3 to 7 millimeters posteriorly to the TKA line. The walking cycle, by definition, will begin at the point of heel contact. As the heel 14 of foot 10 contacts the ground, the coil 82 of ankle 34 will assume the extended position shown in FIG. 2. At the point of "toe off", just before the swing phase of the walking cycle, coil 82 will be at its maximum depression, as shown in FIG. 4. At an intermediate stage of the walking cycle between those stages shown in FIGS. 2 and 4, the spring will assume a neutral position, such as that depicted in FIG. 3. Use of the coil spring gives a degree of control to the wearer of ankle 32 that largely approximates the muscular control a person usually has over a natural foot. The resilient, anterior support provided by this coil is a significant advance over the prior art.

Figures 12, 13, 14:
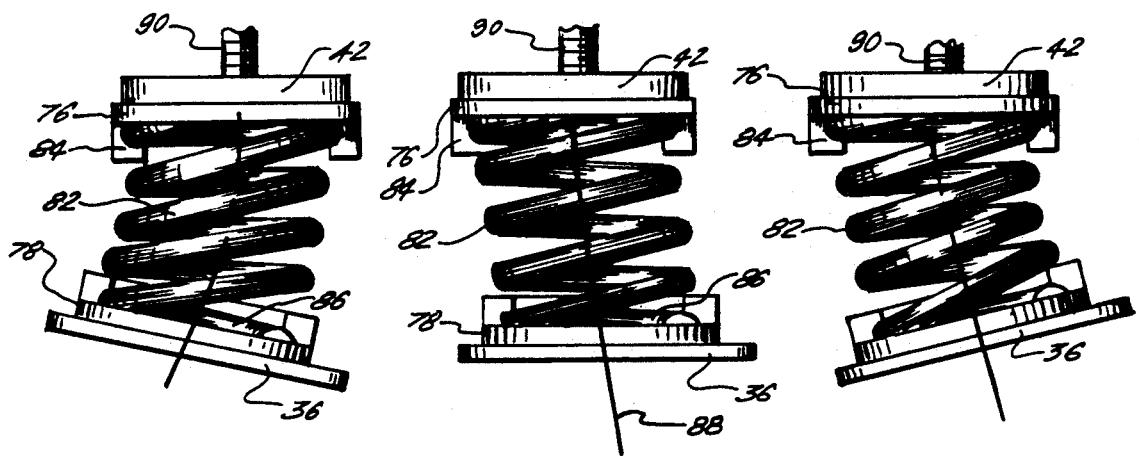
FIGS. 12-14 are successive front views of a right foot ankle undergoing the eversion-inversion process.

At the beginning of the walking cycle, inversion occurs as shown in FIG. 14. During the arc-like transfer of weight from the lateral to the medial aspect of the sole, the plate 36 will pass through a substantially flat, intermediate position as shown in FIG. 13. Progressive eversion then occurs until plate 36 assumes a position similar to that shown in FIG. 12.

Lateral rotation is also occurring simultaneously with dorsiflexion-plantar flexion and inversion-eversion to provide smooth movement of the ankle 34, thereby imitating the natural movements of a human ankle.

Figure 15:
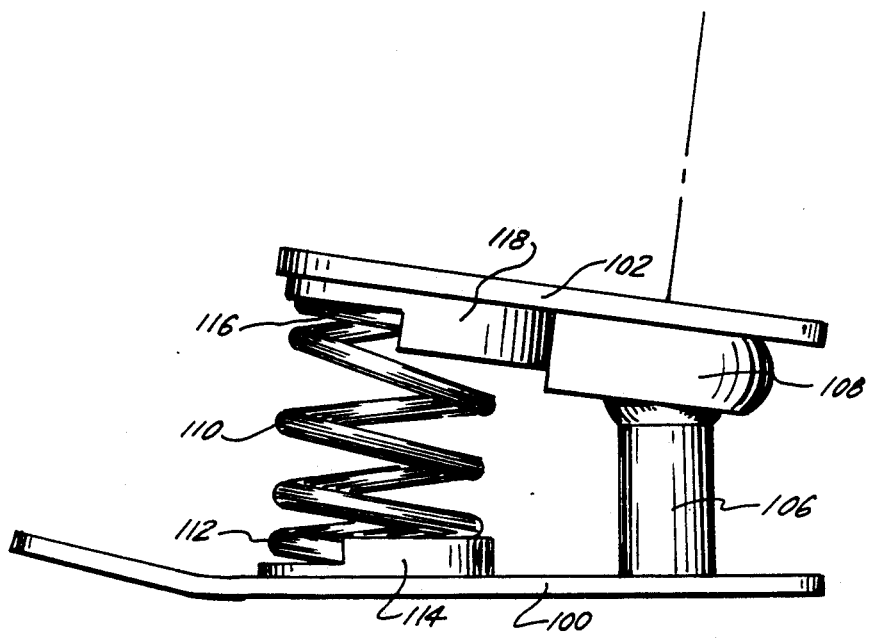
FIG. 15 is a side elevational view of a second embodiment of the present invention showing the spring in an extended position.
Figure 16:
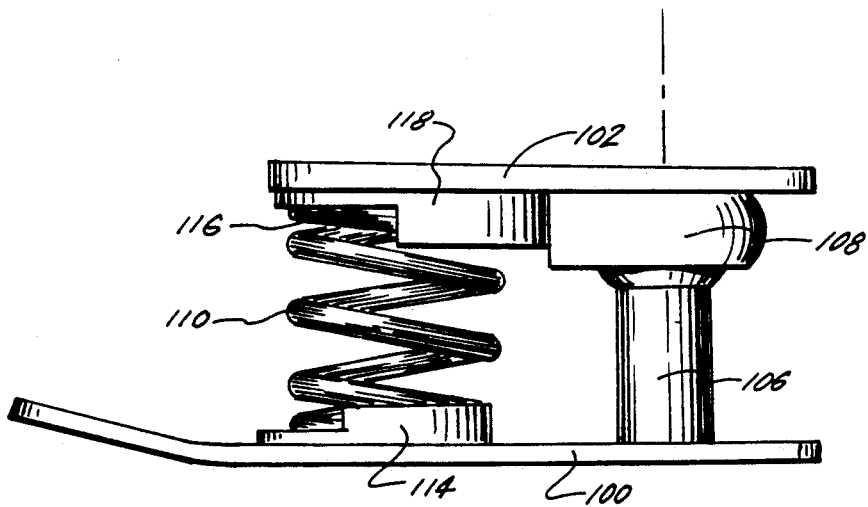
FIG. 16 is a view similar to FIG. 15 showing the spring in a neutral position.
Figure 17:
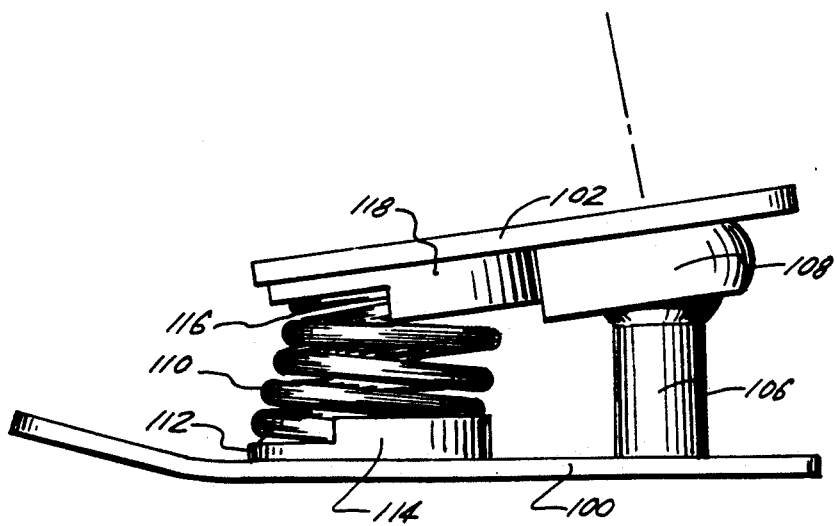
FIG. 17 is a view similar to FIGS. 15-16 showing the spring in a compressed position.

A second, less preferred embodiment of the invention is shown in FIGS. 15-17. This embodiment is similar to that shown in FIGS. 1-8 and 11-14. A substantially flat, rectangular sole plate 100 is elongated along the longitudinal axis of the foot and is adapted for attachment to an elongated base embedded in the artificial foot (not shown, but similar to base 28 described above). A substantially rectangular limb supporting plate 102 is elongated along the longitudinal axis of the foot and held in spaced, substantially parallel relationship to plate 100. Plates 100, 102 are made of steel and are of appropriate dimensions to fit within an artificial foot. Plate 100 is provided with an upwardly inclined toe 104.

Figure 9:
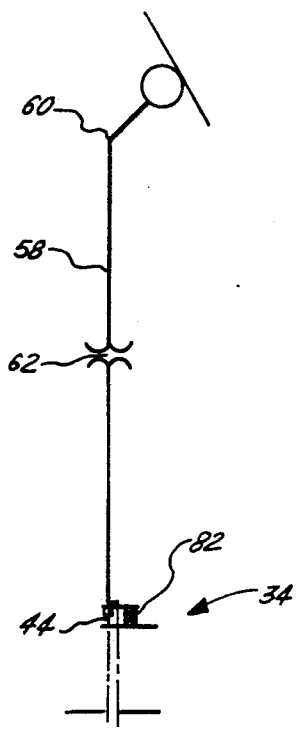
FIG. 9 is a schematic diagram illustrating the trochanter-knee-ankle line and its relationship to the parts of the biomechanical ankle.
Figure 7:
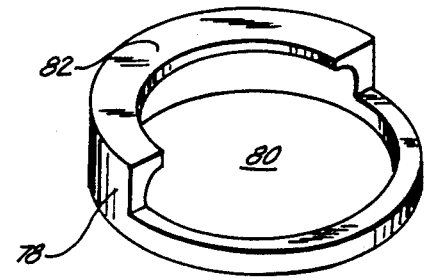
FIG. 7 is a perspective view of one of the collars fixed to the opposing plates in the ankle in which the edges of the spring are fixed.

Plates 100, 102 are held in spaced, substantially parallel relationship by an upright post 106 that is positioned for placement substantially colinearly with the trochanter-knee-ankle line of an amputee (see FIG. 9). The post 106 and plate 102 are coupled with a ball and socket joint 108. The most natural point for placement of post 106 is 3-7 mm posterior to the TKA line.

A helical spring coil 110 is disposed anterior to post 106 and is disposed in fixed engagement between plates 100, 102. The inferior edge 112 of coil 110 is fixed to plate 100 in a lower collar 114 which is provided with an internal groove (not shown) in which edge 112 is fixedly disposed. Superior edge 116 of coil 110 is fixed to plate 102 in similar fashion, being fixedly disposed within an internal groove of upper collar 118. The longitudinal axis of coil 110 is offset from a vertical plane by 5°-10°, superior edge 116 of spring 110 inclining toward the medial aspect of the amputee's body.

A threaded stud (not shown) similar to stud 90 disposed in a longitudinal slot may be used to affix the ankle shown in FIGS. 15-17 to an amputee or artificial limb. However, a fixed stud may also be used.

Having described my invention, what I claim as new and desire to secure Letters Patent for is:

1. A biomechanical ankle for use in an artificial foot adapted for attachment to an amputee, said ankle comprising:
   a. a substantially flat sole plate adapted for attachment to said artificial foot;
   b. a limb supporting plate held in spaced, substantially parallel to said sole plate by an upright post that is positioned for placement substantially colinearly with the trochanter-knee-ankle line of said amputee, a joint member disposed between at an upper end portion of said post and the limb supporting plate, said joint member rotatably coupling the post to the limb supporting plate such that the sole plate and the limb supporting plate can rotate in any direction about the post with respect to each other; and
   c. a spring positioned anterior to said post and disposed in fixed engagement between said sole plate and limb supporting plates, one end portion of the spring being fixed to said sole plate and the other end of the spring being fixed to said supporting plate.

2. The biomechanical ankle of claim 1 wherein the spring having a longitudinal axis offset from the vertical plane by 5 degrees-10 degrees with a superior end of the spring being inclined toward the medial aspect of said amputee body.

3. The biomechanical ankle of claim 1 further provided with adjustment means for selectively adjusting the position of attachment between said supporting plate and the amputee.

4. The biomechanical ankle of claim 3 wherein said adjustment means is comprised of a screw threaded stud with an enlarged head, said head being disposed in sliding engagement within an elongated longitudinal slot in said supporting plate, the diameter of said head being greater than the width of said slot, said stud extending upwardly from the surface of said supporting plate.

5. The biomechanical ankle of claim 1 wherein said sole plate is fixed to a base member embedded in said artificial foot.

6. The biomechanical ankle of claim 5 wherein said sole plate and support plate are substantially rectangular and elongated along the longitudinal axis of the foot, said supporting plate having a length that is less than the length of said sole plate.

7. The biomechanical ankle of claim 1 wherein said upright post is positioned for placement 3-7 mm posterior to the trochanter-knee-ankle line of said amputee.

8. A biomechanical ankle for use in an artificial foot adapted for attachment to an amputee, said ankle comprising:
- a substantially flat rectangular sole plate elongated along the longitudinal axis of the foot and adapted for attachment to an elongated plate embedded in said artificial foot;
- a substantially flat rectangular limb supporting plate elongated along the longitudinal axis of the foot and held in spaced, substantially parallel relationship to said sole plate by an upright post that is positioned for placement substantially colinearly with the trochanter-knee-ankle line of said amputee, said post and limb supporting plate being coupled with a universal joint;
- a helical coil anterior to said post and disposed in fixed engagement between said sole plate and limb supporting plates, the inferior edge of the coil being fixed to said sole plate and the superior edge of the coil being fixed to said supporting plate, the longitudinal axis of said coil being offset from the vertical plane by 5 degrees-10 degrees, the superior edge of said spring inclining toward the midline of said amputee's body; and
- a screw threaded stud with an enlarged head for attaching the artificial foot and ankle to the amputee, said head being disposed in sliding engagement within an elongated longitudinal slot in said support plate, the diameter of said head being greater than the width of said slot, said stud extending upwardly from the surface of said supporting plate.

9. The biomechanical ankle of claim 8 wherein said upright post is positioned 3-7 millimeters posterior to the trochanter-knee-ankle line of said amputee.

* * * * *